United States Patent [19]

Keller

[11] Patent Number: 5,078,689

[45] Date of Patent: Jan. 7, 1992

[54] DEVICE FOR REMOVING BODY FLUIDS

[76] Inventor: Alan M. Keller, 1353 E. 26th Pl., Tulsa, Okla. 74114

[21] Appl. No.: 523,395

[22] Filed: May 14, 1990

[51] Int. Cl.$^5$ ............................................. A61M 5/178
[52] U.S. Cl. ..................... 604/167; 604/93; 604/164; 604/174
[58] Field of Search ............. 604/19, 27, 48, 93, 604/158, 161–170, 174, 264, 272; 606/108; 128/760, 763, 768, 770

[56] References Cited

U.S. PATENT DOCUMENTS

| | | | |
|---|---|---|---|
| 3,916,903 | 11/1975 | Pozzi | 604/164 X |
| 4,419,094 | 12/1983 | Patel | 604/93 |
| 4,496,348 | 1/1985 | Genese et al. | 604/167 |
| 4,531,937 | 7/1985 | Yates | 604/164 X |
| 4,778,452 | 10/1988 | Moden et al. | 604/93 |
| 4,842,591 | 6/1989 | Lutner | 604/283 |
| 4,973,312 | 11/1990 | Andrew | 604/158 |

Primary Examiner—C. Fred Rosenbaum
Assistant Examiner—Corrine Maglione
Attorney, Agent, or Firm—Head & Johnson

[57] ABSTRACT

This is a medical device useful for removing fluids from body cavities. A flexible catheter is attached to a stabilizing base with a collar forming a vestibule on the opposite side of the base. The vestibule is sealed with a stopper or diaphragm. A needle is inserted through the stopper, into the diaphragm, through a central hole in the base and through the lumen of the catheter and out the terminal hole of the catheter. After insertion into the body, the needle is withdrawn leaving the catheter and base in place for drainage. The unit is a self sealing structure to prevent introduction of contamination of ambient air.

7 Claims, 3 Drawing Sheets

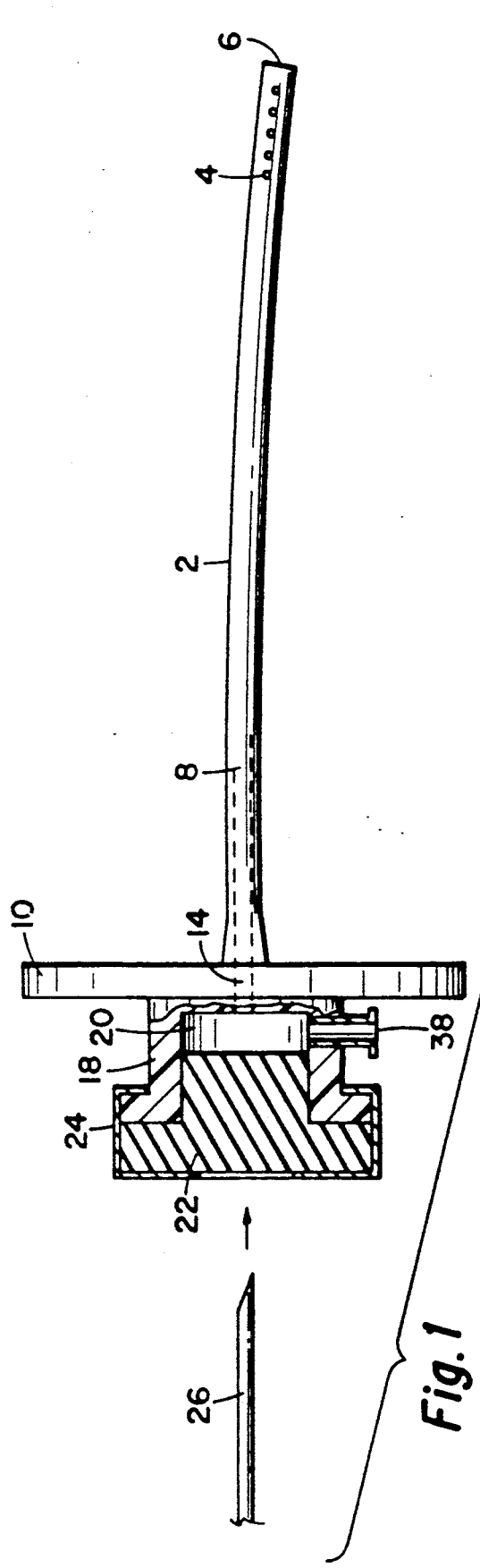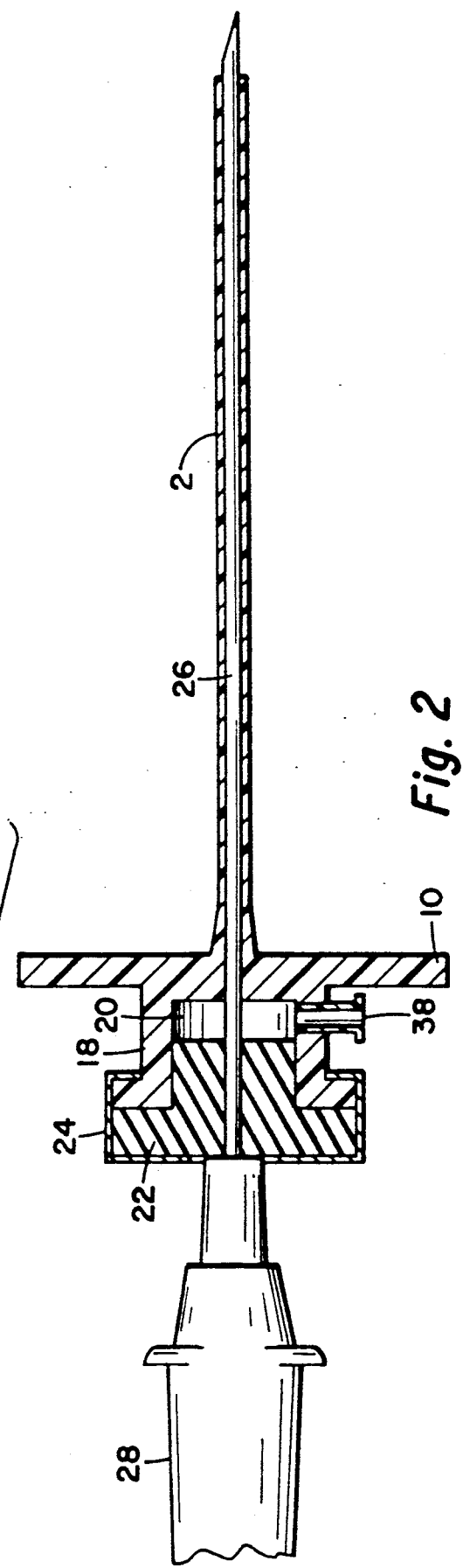

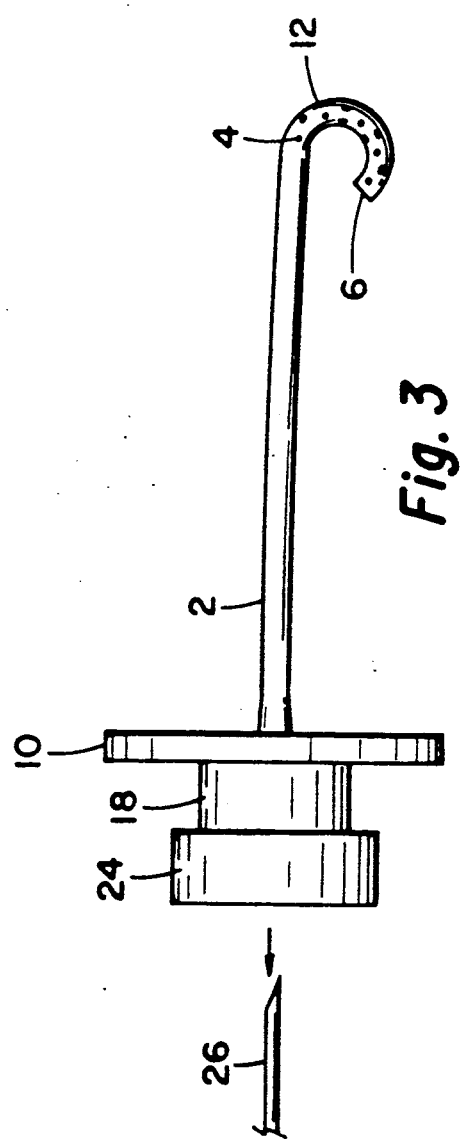

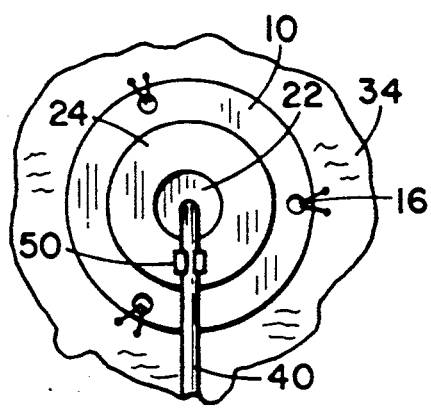
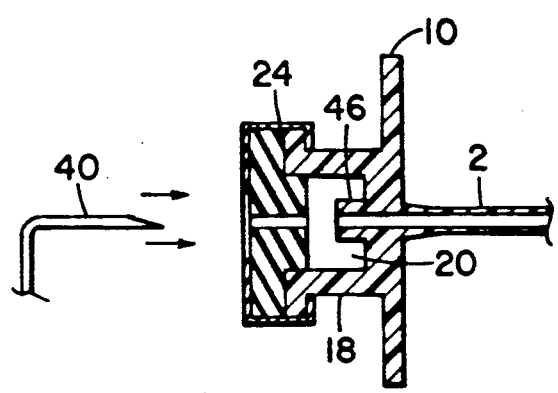
Fig. 8          Fig. 5
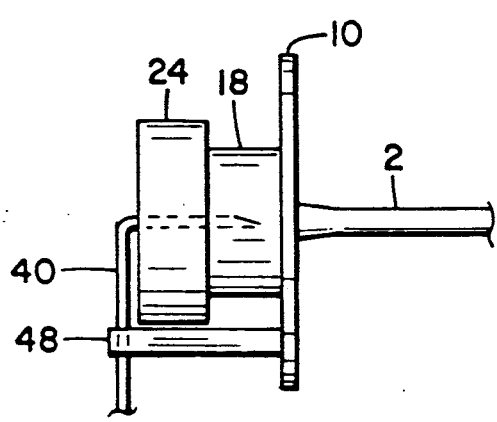
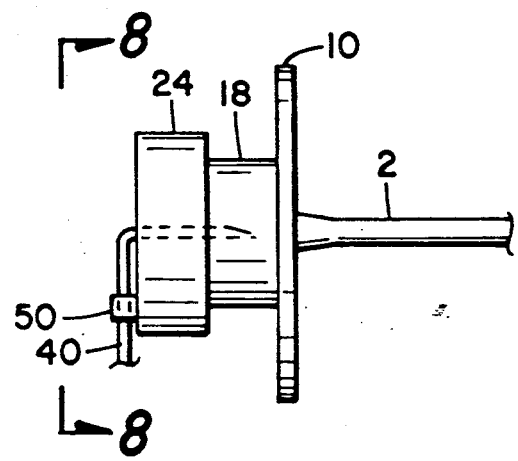
Fig. 7          Fig. 6
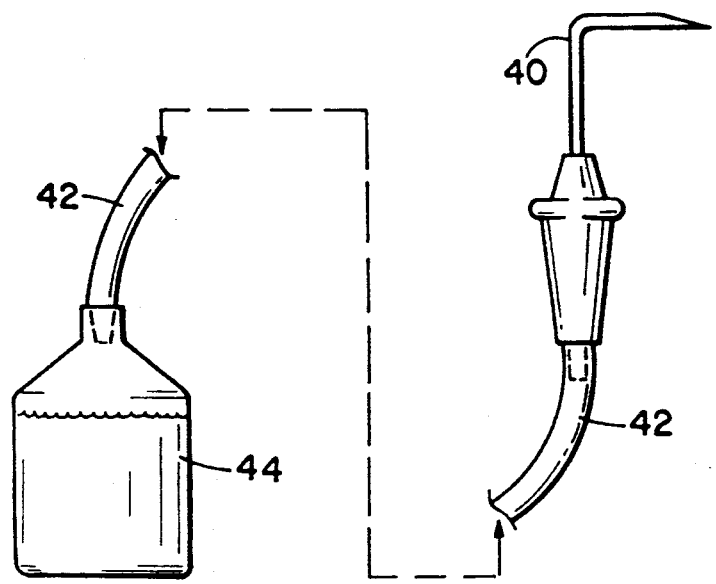
Fig. 9

DEVICE FOR REMOVING BODY FLUIDS

SUMMARY OF THE INVENTION

This is a medical device used to enter a body cavity and to drain fluid from the cavity by a flexible means and with a self sealing feature forming a closed drainage system.

Thoracentesis (removal of fluid from the chest cavity) and paracentesis (removal of fluid from the abdominal cavity) are often necessary for diagnostic or for therapeutic purposes. Both procedures carry risks including, but not limited to bleeding, infection, and discomfort. The greatest risk and most common complication, however, is the inadvertent puncture of the lung leading to a totally or partially collapsed lung (pneumothorax). Pneumothorax can also occur if air enters the thoracic cavity through an open needle or catheter which has been placed into the thoracic cavity. If pneumothorax does occur, a chest tube must be placed into the chest cavity and attached to a suction device for several days in order to re-expand the lung by maintaining negative pressure, a complicating pneumothorax usually leads to several days of hospitalization with additional risks and expenses.

Pneumothorax is seen all too often with thoracentesis as the amount of fluid in the thorax decreases and the lung re-expands downward toward the location of the sharp-tipped needle which has been introduced into the chest cavity between the ribs. When the lung reaches the sharp immobile needle tip, a puncture of the lung occurs with resultant pneumothorax. Experienced physicians, therefore, do not attempt removal of all of the fluid for fear of pneumothorax. As a result, the procedure may need to be repeated more frequently, leading to increased numbers of physicians visits, X-rays, expenses and risks.

Essentially the same discussion applies to paracentesis. The presence of a sharp object in the abdominal cavity may lead to puncture of one of the hollow organs of the gastrointestinal tract. As with the lung, as the fluid volume decreases, the risk of puncture increases.

Another problem encountered with the use of needles or catheters introduced into the body cavity, is that these are open-ended and may allow external air or contaminates to enter the body cavity.

Others have devised types of catheters and reference may be had to the following U.S. Pat. Nos. 3,030,953; 3,612,050; 3,739,778; 4,424,833; 4,496,348; 4,610,674; 4,629,450; 4,643,712; 4,475,548.

DESCRIPTION OF THE DRAWINGS

FIG. 1 is a longitudinal sideview of the device of this disclosure shown partially in cross-section with the guide needle ready for insertion.

FIG. 2 is a longitudinal cross-sectional sideview of the device with the guide needle inserted and attached to a syringe.

FIG. 3 is a longitudinal sideview of the device with a pig-tail type catheter.

FIG. 4 is a longitudinal cross-sectional sideview of the device with a guide wire attached to the plunger in the syringe and extending into the guide needle.

FIG. 5 is a cross-sectional side view of the vestibule of the device with an annulus around the central hole of the stabilizing base to provide support for the drainage needle.

FIG. 6 is a sideview of the collar and retaining band showing the collar clip holding the drainage needle.

FIG. 7 is a sideview of the stabilizing base and collar showing a base support clip holding the drainage needle.

FIG. 8 is a topview of the device attached to the skin of a patient with a drainage needle in place and attached to the collar clip.

FIG. 9 is a sideview of the drainage system as used with the device.

DESCRIPTION OF THE PREFERRED EMBODIMENTS

The present disclosure uses a flexible catheter with multiple drain holes for draining fluid from body cavities. The disclosure forms a closed system allowing no ambient air or contaminates into the body cavity.

FIG. 1 is a side view of one embodiment of the invention. A flexible catheter 2, with multiple drain holes 4, a terminal hole 6 and a central lumen 8, is attached to a stabilizing base 10. The catheter may be formed of latex, teflon, silastic, polyurethane, plastic or any other suitable flexible material. Various catheter shapes and sizes may also be used, such as a terminal pig-tail configuration 12 as shown in FIG. 3.

The supporting base 10 has a central hole 14 to which the catheter is hermetically sealed; such that the lumen 8 of the catheter 2 is in unobstructed continuity with the central hole 14 in the stabilizing base 10.

The supporting base 10 is formed of a rigid or semi-rigid material, such as plastic or metal. The periphery of the base 10 may have holes 16 which can be used to suture or secure the base to the skin 34 or other support.

The opposite side of the base 10, from the catheter 2, has a collar 18 hermetically sealed to the base 10 around the central hole 14 to form a vestibule 20 surrounding the central hole 14. The vestibule is in continuity with the catheter lumen 8 and central hole 14. The collar 18 may be formed of rigid or semi-rigid material, such as metal or plastic.

The top of the collar 18 is sealed with a stopper or diaphragm made of rubber, plastic or other resilient self-sealing material 22. The seal 22 may be held in place by a retaining band 24. This retaining band may be formed of aluminum, plastic or other suitable material.

A guide needle 26 is used to insert the catheter 2. The needle 26 is inserted through the seal 22, into the vestibule 20, through the central hole 14, down the catheter lumen 8 and out the terminal catheter hole 6 with the tip of the needle exposed just beyond the open end of the catheter 6. This guide needle 26 acts as a rigid and sharp means to penetrate the skin, connective tissue, muscle and cavity lining.

In practice, the external end of the guide needle 26 is attached to a syringe 28. The unit is advanced with negative pressure created by pulling on the syringe plunger 30 to create a partial vacuum in the barrel 32. The unit is advanced until the tip enters the body cavity and fluid is aspirated into the syringe. The moment that fluid is aspirated, advancement is halted and the guide needle 26 is held immobile and the catheter 2 is advanced over the needle 26 into the body cavity. As the catheter 2 is advanced, the needle 26 is withdrawn and removed from the unit. The removal of needle 26 from seal 22 allows it to reseal itself preventing any contamination or aspiration of air into the cavity.

The unit is inserted until the base 10 is flush with the skin 34. This forms a low profile with a wide base which offers stability and allows the unit to be left in place for prolonged drainage if necessary. The base 10 may have peripheral holes 16 for suturing to the skin 34.

Variations in the unit would include using a guide wire 36 attached to the plunger 30 of the syringe 28 which could extend through the lumen of the needle 26 to provide a further support for guiding the catheter 2 into the body cavity without advancing the sharp end of the needle. Additionally, the unit may be formed with a sideport 38 in the collar 18. This allows drainage of the vestibule 20. The sideport 38 may be self-sealing with either a rubber or plastic stopper, or a ball-valve (not shown).

The unit, after insertion, is attached to a drainage system. Typically, the drainage system would consist of a large bore drainage needle 40, attached to drainage tubing 42, which is connected to a collection container 44.

The drainage needle 40 may be bent to extend through the seal 22 into the vestibule 20 of the unit. An annulus 46 may be raised around the central hole 14 to accommodate the tip of the drainage needle 40 and to stabilize this needle and keep it from "wiggling."

Other stabilizing means may include a base support clip 48. This would consist on an elongate member firmly attached to the support base 10 and extending upward to grip and hold the drainage needle 40 before it enters the seal 22. A collar support clip 50 may serve the same function. This would be fastened to the collar 18 or the band 24, and would clip onto the drainage needle 40 to provide stability.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An improved catheter apparatus for removing fluid from a body cavity of a patient, comprising:
    a base member having a forward and a rearward surface, the forward surface adaptable to engage an external body surface of a patient, the base having an opening therethrough;
    an elongated tubular catheter having an inner end secured to said base coincident with the said base opening and having an outer end;
    a relatively short tubular collar having a forward end secured to said base rearward surface, the tubular collar being coaxially with said base opening, the tubular collar having a rearward end;
    a seal diaphragm of elastomeric material secured to said collar rearward end normally closing said collar;
    an elongated tubular guide needle of diameter less than the internal diameter of said catheter and of said base member opening, the guide needle having a pointed outer end and being insertable through said seal diaphragm, said base member opening and said catheter whereby the pointed outer end extends past said tubular catheter to form a sharp end for puncturing the body of a patient for insertion of the tubular catheter into a body cavity from which fluid is to be extracted, after which the guide needle may be withdrawn;
    an L-shaped rigid tubular drainage needle having a forward portion and a rearward portion, the forward portion being at a right angle to the rearward portion, the forward portion having a pointed outer end, the forward portion being sealably insertable through said seal diaphragm to establish communication with said tubular catheter, said rearward portion extending adjacent said seal diaphragm and said collar rearward end;
    a flexible drainage tube connected at a first end to said drainage needle rearward portion; and
    a container connected to a second end of said drainage tube for collecting body fluid drained by said catheter.

2. An improved catheter apparatus according to claim 1 wherein said seal diaphragm is dimensioned to provide a vestibule area within said collar between said seal diaphragm and said base, the vestibule area being thereby in communication with said tubular catheter through said base opening, and wherein said drainage needle pointed outer end extends within the vestibule area when said drainage needle forward portion is inserted through said seal diaphragm.

3. An improved catheter apparatus according to claim 1 wherein said drainage needle forward portion is of diameter less than said opening in said base member and wherein said outer pointed end of said drainage needle forward portion extends within said base member opening when said drainage needle forward portion is inserted through said seal diaphragm.

4. An improved catheter apparatus according to claim 1 wherein said seal diaphragm is secured to said collar rearward end by a circumferential retaining band.

5. An improved catheter apparatus according to claim 1 including means of retaining said drainage needle forward portion in communication with said tubular catheter after said forward portion has been inserted through said seal diaphragm.

6. An improved catheter apparatus according to claim 5 wherein said means of retaining said drainage needle includes a retaining clip affixed to said base member or said collar and removably receiving said drainage needle rearward portion.

7. An improved catheter apparatus according to claim 1 wherein said base member has holes for use in attachment of the base member to the body of a patient.

* * * * *